United States Patent
Böhling et al.

(10) Patent No.: US 7,253,322 B2
(45) Date of Patent: Aug. 7, 2007

(54) METHOD FOR PRODUCING ETHYLDIMETHYLAMINE AND TRIETHYLAMINE

(75) Inventors: Ralf Böhling, Griesheim (DE); Ulrich Steinbrenner, Neustadt (DE); Frank Funke, Frankenthal (DE); Günter Müller, Ludwigshafen (DE); Günter Gaus, Biblis (DE); Christoph Benisch, Mannheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 510 days.

(21) Appl. No.: 10/506,514

(22) PCT Filed: Mar. 3, 2003

(86) PCT No.: PCT/EP03/02167

§ 371 (c)(1),
(2), (4) Date: Sep. 3, 2004

(87) PCT Pub. No.: WO03/074468

PCT Pub. Date: Sep. 12, 2003

(65) Prior Publication Data

US 2005/0154235 A1    Jul. 14, 2005

(30) Foreign Application Priority Data

Mar. 4, 2002    (DE) ............................ 102 09 528

(51) Int. Cl.
*C07C 209/60* (2006.01)

(52) U.S. Cl. ...................................... 564/485; 564/469
(58) Field of Classification Search ..................... None
See application file for complete search history.

(56) References Cited

U.S. PATENT DOCUMENTS

| 2,750,417 A | 6/1956 | Closson et al. ............. 260/577 |
| 4,302,603 A | 11/1981 | Pez ............................ 564/485 |
| 4,336,162 A | 6/1982 | Pez ............................ 252/438 |

OTHER PUBLICATIONS

Howk et al., "*Alkali Metal-Ccatalyzed Amination of Olefins*", J. Am. Chem. Soc. 76, 1899-1902 (1954).

*Primary Examiner*—Brian Davis
(74) *Attorney, Agent, or Firm*—Novak Druce & Quigg, LLP

(57) ABSTRACT

The present invention describes a process for the preparation of ethyldimethylamine and triethylamine with the following steps:
 (i) reaction of a mixture of diethylamine and dimethylamine with ethylene in the presence of a catalyst from the group of alkali metal dimethylamides, alkali metal diethylamides and alkali metal hydrides
 (ii) removal of the catalyst
 (iii) distillation separation of the resulting mixture in triethylamine and ethyldimethylamine and optionally diethylamine and dimethylamine
 (iv) optional return of the catalyst and of the starting amines to the reaction.

The process according to the invention permits the coproduction of ethyldimethylamine and diethylamine in a simple process.

14 Claims, No Drawings

METHOD FOR PRODUCING ETHYLDIMETHYLAMINE AND TRIETHYLAMINE

This application is a 371 of PCT/EP03/02167 filed Mar. 3, 2003.

The present application relates to a process for the preparation of ethyldimethylamine and triethylamine.

Triethylamine serves as a starting material for the preparation of surfactants, textile and flotation auxiliaries, bactericides, corrosion and foam inhibitors, additives for pharmaceuticals, and as antioxidants for fats and oils. Said amine can be prepared by the hydrogenation of corresponding nitrites or nitro compounds, by the reductive amination of corresponding aldehydes and ketones and by the amination of corresponding alcohols. In particular, it is prepared on an industrial scale by the amination of the corresponding alcohol or of the corresponding carbonyl compound over metal catalysts, which may be supported, under hydrogenating conditions.

Ethyldimethylamine is likewise an important industrial product. It is used for the most part in the casting industry, in the so-called cold-box process. Small amounts are used in the pharmaceutical industry.

The use of aldehydes, ketones and nitrites and also of alcohols, i.e. in the present case ethanol, as starting material for the preparation of alkylamines is uneconomical compared with the use of the corresponding olefin, i.e. ethene, principally due to the cost of the starting materials.

One alternative for the preparation of said amines consists in the addition of $NH_3$ or amines onto ethylene in the presence of acidic catalysts, such as, for example, zeolites, basic catalysts, such as, for example, metal amides, in particular alkali metal and alkaline earth metal amides, amides of subgroup IV, alkali metal alkoxides, or of transition metal complex compounds.

This so-called hydroamination of olefins, however, has a number of difficulties which often stand in the way of an industrial application of the reaction. Examples thereof are listed below.

Thus, in the case of the $NaNH_2$— or $KNH_2$-catalyzed addition of NH3 onto olefins, as is described, for example, in B. W. Howk et al., J. Am. Chem. Soc. 76 (1954), 1899-1902 and R. D. Closson et al., U.S. Pat. No. 2,750,417, the space-time yields of desired alkylamines are very small even at high temperatures and olefin pressures due to the low activity and solubility of the metal amide. U.S. Pat. Nos. 4,336,162 and 4,302,603 describe a solution approach to this problem by changing to the Rb and Cs amides or by using a eutectic of $NaNH_2$ and $KNH_2$. In the first case, industrial realization is precluded due to the extremely high catalyst cost, and in the second case the space-time yields of desired alkylamines are still too small.

The hydroamination of olefins with secondary amines in the presence of acidic catalysts again generally proceeds in poorer yields and with poorer selectivities than the corresponding hydroamination with ammonia or primary amines.

It is an object of the present invention to provide a process with which ethyldimethylamine and trimethylamine can be prepared in one process, where the desired amounts of prepared ethyldimethylamine and triethylamine can be controlled.

We have found that this object is achieved by a process for the preparation of ethyldimethylamine and triethylamine with the following steps:
(i) reaction of a mixture of diethylamine and dimethylamine with ethylene in the presence of a catalyst from the group of alkali metal dimethylamides, alkali metal diethylamides and alkali metal hydrides
(ii) removal of the catalyst
(iii) distillation separation of the resulting mixture in triethylamine and ethyldimethylamine and optionally diethylamine and dimethylamine
iv) optional return of the catalyst and of the starting amines to the reaction.

The process according to the invention permits the preparation of ethyldimethylamine and triethylamine in a process in which a coproduction of ethyldimethylamine and triethylamine is carried out where, using simple process steps, the preparation of these amines can take place in a single process. Since ethyldimethylamine and triethylamine can be separated easily from one another by distillation and from diethylamine or a diethylamine/dimethylamine mixture, the process according to the invention is advantageous compared with the separate production of the two amines. Here, recourse is made to diethylamine and dimethylamine as starting material for the reaction.

The applications DE 100 30 619.5 and DE 100 41 676.4 by the applicant describe a general process for the preparation of amines by hydroamination of olefins. In this process, in a first process stage, an olefin is reacted
a) with a primary amine or with a secondary amine in the presence of a metal monoalkylamide or metal dialkylamide as catalyst or
b) with ammonia or a primary amine in the presence of an inorganic solid-body acid as catalyst or
c) with ammonia, a primary amine or a secondary amine in the presence of a transition metal complex compound as catalyst and then the resulting hydroamination product(s) is/are reacted in the second process stage either in the presence of a transalkylation catalyst or in the presence of hydrogen and a transalkylating hydrogenation or dehydrogenation catalyst at temperatures of from 80 to 400° C.

It is not disclosed in these applications to use ethylene with diethylamine and dimethylamine in a process together for the preparation of the corresponding ethyl- and methyl-containing amines.

The process according to the invention is described more precisely below.

In the first process stage, ethylene is reacted with diethylamine and dimethylamine under hydroaminating conditions. The addition of ethylene onto the respective amine produces triethylamine and ethyldimethylamine.

Through the relative amount of the ethylene (partial pressure) and the amount of the amines, it is possible to control the distribution of the resulting products relative to one another.

Dimethylamine reacts with ethylene to give a product which is more stable than diethylamine. Thus, if a mixture of diethylamine/dimethylamine is present, the amount of dimethylamine present reacts initially with ethylene completely or virtually completely before triethylamine is formed. The product composition of the resulting mixture can thus be controlled in a simple manner via the composition of the starting mixture, a substoichiometric amount of ethylene bringing about an incomplete conversion of diethylamine.

If the process according to the invention is to be used to prepare product mixtures which, in addition to the products ethyldimethylamine and triethylamine and optionally present secondary products, no longer contain diethylamine, an excess of ethylene is used in the hydroamination reaction.

If a certain proportion of diethylamine is to remain, then a substoichiometric amount of ethylene is used.

Generally, the hydroamination according to the present invention is carried out in such a way that the amine from which the alkylamine to be prepared in preference arises is used in excess compared with the other starting material. Since there is generally a greater requirement for triethylamine, the starting materials diethylamine and dimethylamine are preferably used in a ratio of from (8 to 15): 1, in particular in a ratio of 10:1, so that triethylamine and ethyldimethylamine are also obtained in such a ratio. This usually corresponds to market demand. The ratios of diethylamine and diethylamine to be used can, however, be tailored in a flexible manner to correspond to the requirement of the respective products, which constitutes a further advantage of the process according to the invention.

In addition, a significant excess of ethylene is preferably added.

The hydroamination according to the invention using diethylamine and dimethylamine is preferably carried out in one reaction stage, the product distribution being adjusted as illustrated above via the feed amounts of the starting materials.

The hydroamination according to the invention is carried out using an alkali metal hydride or amides of the alkali metals as catalyst.

The hydrides and amides which can be used here are salts of Li, Na, K, Rb or Cs, preferably of Li, Na or K, in particular of Na. The most preferred hydride is thus NaH.

The amides used according to the invention are diethylamide, dimethylamide and/or ethylmethylamide. Preference is given to using diethylamide or dimethylamide or a mixture of the two in any desired ratio. Particular preference is given to Na diethylamide, Na dimethylamide or mixtures thereof.

The metal amides can be introduced into the reaction according to the invention as such, for example in the form of a solution, it being possible for the metal amides to originate from any desired source.

In a preferred embodiment of the present invention, the metal amide is prepared prior to introduction into the reaction from the corresponding amine, i.e. dimethylamine, ethylmethylamine or diethylamine. The metal amides are prepared here in accordance with methods known from the literature. These are described, for example, in Houben-Weyl, Methoden der organischen Chemie [Methods of organic chemistry], 4th edition, volume XI/2, Thieme Verlag, Stuttgart, pages 182ff U.S. Pat. No. 4,595,779, WO-A 93/14061, DE-A-21 17 970, German Reichspatent 615,468, GB-A 742 790, DE-A 26 13 113, U.S. Pat. No. 2,750,417, J. Wollensak, Org. Synth. 43 (1963), pages 45ff, and C. A. Brown, J. Am. Chem. Soc. 95 (1973), pages 982ff. In general, the preparation of the amide is carried out either by reacting an alkali metal with the corresponding amine in the presence of an unsaturated compound, such as, for example, butadiene, isoprene, naphthalene, pyridine or styrene as electron carrier, by reacting a metal amide or hydride with the corresponding amine or reacting an organometallic compound, for example n-BuLi, MeLi, PhNa, $Et_2Mg$ or $Et_4Zr$, with the corresponding amine.

In the preparation from amine and alkali metal, alkali metal in technical grade is generally used which is contaminated by up to 10% by weight of oxides, hydroxides, calcium and the other alkali metals. Other elements may be present in traces (>1% by weight), although these are generally not troublesome, even at higher concentrations. It is of course also possible to use prepurified alkali metal which does not have the mentioned impurities, or has them only in traces. For cost reasons, however, preference is generally given to technical-grade alkali metal. It is possible to use all alkali metals, preference being given to using Li, Na or K, more preference being given to Na or K, in particular Na. Where appropriate, it is also possible to use mixtures of the alkali metals.

Prior to the addition of the amine, the alkali metal is, in one embodiment of the present invention, dispersed in a suitable inert solvent. The inert solvents used are preferably saturated hydrocarbons, preferably low-boiling paraffins, such as n-butane, i-butane, pentanes and hexanes, cyclohexane and mixtures thereof or high-boiling paraffins comprising optionally branched and saturated cycloparaffins, for example white oil.

The solvents mentioned are usually industrial in origin and can also comprise acidic impurities, such as, for example, water, aldehydes, ketones, amides, nitrites or alcohols in small amounts.

The dispersion can take place above the melting temperature of the alkali metal using, for example, a suitable stirrer, a jet nozzle, a reaction mixing pump or a pump and a static mixer. The alkali metal can also be squirted into cold solvent or be sprayed from the gas phase onto cold solvent. Spraying into cold gas with subsequent redispersion is also possible.

Further options involve dispersing the alkali metal in a mixture of inert solvent and starting amine, or dispersing the alkali metal in the solvent(s) and adding the corresponding starting amine. A further option, finally, involves dispersing the alkali metal in the product amine(s) and adding the corresponding amine. Where appropriate, a separate device is used for the dispersion operation, for example a stirred reactor, a jet nozzle or a reaction mixing pump.

For the preparation of the amide, the alkali metal is generally introduced in the form of fine particles. In the case of sodium, these particles preferably have a size distribution such that 50% by weight of the particles are of a size <1000 µm, more preferably <300 µm, in particular <100 µm.

In one embodiment of the present invention, the alkali metal is dispersed in a paraffin and, prior to introducing the alkali metal into the reaction, at least a large part of this paraffin is decanted off and replaced by trialkylamine and/or dialkylamine.

An electron carrier, in particular 1,3-butadiene, either alone or in a mixture with the starting dialkylamine, is then metered in. Alternatively, a simultaneous addition of the electron carrier and of the dialkylamine is also possible.

The salt formation to give the amide thus proceeds in the presence of a suitable unsaturated compound, for example butadiene, isoprene, naphthalene, pyridine or styrene. In a preferred embodiment of the present invention, the unsaturated compound used is butadiene or isoprene, particularly preferably 1,3-butadiene.

In the preparation of the amide catalyst from elemental metal, preferably Na, a temperature of from 0 to 150° C., preferably 20 to 90° C., in particular 30 to 70° C., and a pressure of from 1 to 200 bar, preferably 1 to 100 bar, in particular 3 to 50 bar, is maintained. The amide preparation can be carried out batchwise, semicontinuously or continuously.

The above-described catalyst systems suitable for carrying out the reaction according to the invention can be used in solution, as suspension or applied to a support.

Diethylamine and dimethylamine are, after providing the catalyst, reacted with ethylene. This gives a mixture of ethyldimethylamine and triethylamine. The relative amount of the organoamines formed can be controlled via the amount of starting material. After hydroamination has taken place, the resulting amine mixture is separated as described below.

In the hydroamination, ethene is hydroaminated with diethylamine and dimethylamine in the presence of catalytic amounts of an alkali metal diethyl- or dimethylamide or a mixture thereof or an alkali metal hydride. The streams passed to the reactor comprise 0 to 1% by weight, preferably <0.1% by weight, of ammonia, 0 to 5% by weight, preferably <1% by weight, of monoethylamine and monomethylamine, 20 to 80% by weight, preferably 40 to 70% by weight, of (diethylamine+dimethylamine), 0 to 50% by weight, preferably <40% by weight of triethylamine, 5 to 50% by weight, preferably 10 to 30% by weight, of ethylene, 0.01 to 20% by weight, preferably 0.1 to 2% by weight, of the catalyst and 0 to 20% by weight of a solvent for the catalyst.

In a batchwise process, these stream data correspond to the starting concentrations in the reactor.

The reaction can be carried out in diverse reactors, for example in a bubble column (preferably cascaded), a stirred reactor, a jet loop reactor or a reactor cascade. The reaction is carried out at 40 to 150° C. and 1 to 100 bar, in particular at 70 to 120° C. and 5 to 40 bar. The catalyst is preferably present in homogeneously dissolved form in the liquid phase. In principle, the reactor can also be operated in suspension method if the solubility of the catalyst is exceeded.

The reaction discharge is worked up using the methods known to the person skilled in the art, preferably by distillation, in a manner such that the low-boiling components (ethene, dimethylamine), the high-boiling components (catalyst, triethylamine), and diethylamine are separated off from the reaction discharge and returned to the reactor. The products which arise as medium-boiling components (triethylamine, ethyldimethylamine) are separated and removed from the process.

In a batchwise version of the process, the addition products formed are preferably distilled off directly from the reactor. The catalyst can, provided it has adequate activity, remain in the reactor and can thus be utilized for further conversions.

In the continuous version of the process, the adducts formed (triethylamine, ethyldimethylamine) can be removed from the reaction mixture, for example, by stripping with unreacted ethene. The reaction mixture is, however, preferably passed to a flash evaporation or directly to a distillation. Here, the catalyst, which is preferably dissolved in a high-boiling solvent (>50% by weight) or in trialkylamine (>50% by weight) and is produced at the bottom of the column or in the liquid phase of the evaporator, is, in a preferred embodiment, returned to the reactor. A partial stream is disposed of to remove high-boiling components and catalyst. As an alternative to the thermal work-up of the reaction discharge, a filtration can be used to recycle or retain the catalyst. The low-boiling and medium-boiling components are worked up in a suitable distillation sequence known to the person skilled in the art, where ethene, dimethylamine and diethylamine are returned to the reactor.

Parts of the ethene dissolved in the reaction discharge can preferably be firstly separated from the reaction discharge in a flash evaporation and be returned directly to the reactor via a compression unit. The reaction discharge which remains is processed as described above.

In the hydroamination reactions, inert alkylamines and also saturated hydrocarbons may be present in the reactor. However, since they hinder distillative separation of the product mixture, the presence of these compounds is not preferred.

In a preferred embodiment of the present invention, the preparation of the amide and the hydroamination are carried out in a single process stage.

In this embodiment, one of the amines to be alkylated, or a mixture of these amines in the desired ratio with the amount of Na required for forming the necessary amount of amide, is advantageously firstly reacted in the presence of an electron-carrying compound, preferably butadiene. As a result of the presence of the electron carrier, the formation of the amide spontaneously starts. The excess of the amine or of the amines which is not reacted with the Na to give the amide reacts with ethylene to give the desired product.

The amount of Na which is used in the amide preparation is chosen such that a molar ratio of Na to the total amount of ethylene of from 1:5 to 500, preferably from 1:10 to 1:200, in particular from 1:50 to 1:150, is present.

If the amide preparation and the hydroamination are carried out in a combined manner as described above, this takes place at temperatures of from 0 to 150° C., preferably 20 to 90° C., in particular 30 to 70° C., and pressures of from 1 to 200 bar, preferably 1 to 100 in particular 3 to 50 bar.

In most cases, the product primarily desired is triethylamine. In these cases, an excess of diethylamine, based on dimethylamine, will be used. The excess of diethylamine and optionally also the amount of ethylene is here preferably adjusted such that triethylamine is formed in an 8- to 15-fold excess, particularly in a 10-fold excess, compared to dimethylethylamine.

The above-described hydroamination of ethylene is carried out at temperatures of from 30 to 180° C., preferably 50 to 100° C. and pressures of from 1 to 200 bar, preferably 20 to 200 bar, in particular 30 to 50 bar.

In all of the above-described reaction variants, the reaction of the olefin with the amine is carried out in the presence of the amide in a manner known to the person skilled in the art. The description of preferred implementation variants can be found in G. P. Pez et al., Pure and Applied Chemistry 57 (1985), pages 1917 -26, R. D. Closson et al., J. Org. Chem. 22 (1957), pages 646 -9, U.S. Pat. No. 2,501,556, D. Steinborn et al., Z. Chem. 29 (1989), pages 333 -4, D. Steinborn et al., Z. Chem. 26 (1986), pages 349 -59 and H. Lehmkuhl et al., J. Organomet. Chem. 55 (1973), pages 215 -20. The reaction of the olefin with the amine in the presence of the metal alkylamide can also be carried out in the presence of smaller amounts of ammonia, generally <1 mol %, based on the amines used, as is described, for example, in DE-A 21 17 970.

The metal alkylamide can be converted to the metal hydride during the reaction as a result of β-elimination or the action of $H_2$ as described in DE-A 26 13 113, where, in the case of the β-elimination, an imine arises. This hydride can be converted back into metal alkylamide and $H_2$, by the action of a primary or secondary amine in accordance with DE-A 26 13 113, C. A. Brown, J. Am. Chem. Soc. 95(3) (1973), 982ff or C. A. Brown, Synthesis (1978), 754ff, meaning that the metal hydride can be regarded as a type of "resting form" of the metal alkylamide. For the purposes of the present invention, therefore, it is to be treated as being equivalent to the metal alkylamide.

In a preferred embodiment of the present invention, a cocatalyst is used which has an acidity of ≦35 on the McEven-Streitwieser-Appleguest-Dessy scale, preferably from 20 to 35, particularly preferably from 25 to 35, very particularly preferably from 30 to 35. The McEven-Streitwieser-Appleguest-Dessy scale is published in D. J. Cram, Fundamentals of Carbanion Chemistry 1965, Acad. Press, NY, chapter 1.

The cocatalysts used are preferably unsaturated nitrogen compounds. These may be imine or the tautomeric enamine compounds. These may be cyclic or open-chain.

Preferred open-chain nitrogen compounds are chosen from open-chain imine or the tautomeric enamine compounds of the formula (I) or (Ia)

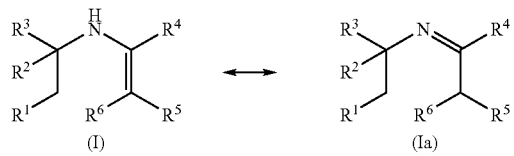

in which the radicals $R^1$ to $R^6$, independently of one another, are hydrogen or alkyl radicals, which may be branched or unbranched and/or interrupted by one or more nitrogen atoms. Preferably, $R^1$ to $R^6$ are $C_1$-$C_{20}$-alkyl radicals, particularly preferably $C_1$-$C_4$-alkyl radicals. Suitable alkyl radicals are, for example, methyl, ethyl, n- or iso-propyl, n- or iso- or tert-butyl.

$R^1$ to $R^6$ may also, independently of one another, be cycloalkyl radicals which may be substituted by the above-mentioned functional groups or by alkyl, alkenyl or alkynyl groups and/or interrupted by one or more nitrogen atoms. Preferred cycloalkyl radicals have 3 to 12 carbon atoms—optionally partially replaced by nitrogen atoms—in their ring, particularly preferably 5 to 6 carbon atoms. The cycloalkyl radicals are very particularly preferably unsubstituted. Particularly suitable cycloalkyl radicals are, for example, cyclopentyl and cyclohexyl.

It is also possible for the radicals $R^1$ to $R^6$, independently of one another, to be alkenyl radicals or alkynyl radicals which have one or more multiple bonds, preferably 1 to 4 multiple bonds. The alkenyl or alkynyl radicals may be substituted corresponding to the alkyl radicals or be interrupted by one or more nitrogen atoms.

It is also possible for two of the radicals $R^1$ to $R^6$ to form a ring together which may in turn be substituted by alkyl, alkenyl or alkynyl groups.

Particularly preferably, the radicals $R^1$ to $R^6$, independently of one another, are hydrogen, methyl or ethyl, where the radicals $R^1$ to $R^6$ are very particularly preferably in each case hydrogen.

Suitable cyclic unsaturated nitrogen compounds are either cyclic enamines or N-heterocyclic compounds in the form of imines or enamines. Preferred cyclic enamines have a $C_4$ to $C_8$-carbon ring, particularly preferably a $C_4$ to $C_6$-carbon ring. This carbon ring is at least monounsaturated and carries at least one amino group which has at least one hydrogen atom. Depending on the size of the ring, the carbon ring may also carry two or more double bonds. Preference is given to using cyclic enamines which are not further conjugated. The carbon ring can be substituted by one or—depending on the size of the ring—more radicals, in addition to the amino group. Suitable radicals correspond to those radicals already given above for $R^1$ to $R^6$, with the exception of hydrogen (within the scope of the substitution of this carbon ring with radicals, a substitution with hydrogen is not thought of as a radical). Preferred radicals are alkyl radicals which may be branched or unbranched and have 1 to 6, particularly preferably 1 to 4, carbon atoms. The number of radicals is dependent on the size of the ring, no to 3 radicals being preferred and the carbon ring particularly preferably carrying no or one, very particularly preferably no, radical. Suitable cyclic unsaturated nitrogen compounds are, for example:

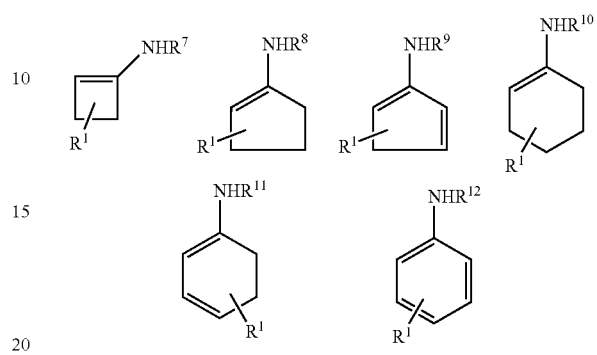

and
double-bond
isomers in which $R^7$ to $R^{12}$ are hydrogen or one of the radicals specified for $R^1$ to $R^6$. $R^7$ to $R^{12}$ are preferably hydrogen, methyl or ethyl radicals, very particularly preferably hydrogen or ethyl radicals.

R' can represent a single substituent or two or more substituents on the carbon ring, where the maximum number of radicals R' corresponds to the number of hydrogen atoms of the ring carbon atoms. The number of radicals R' is preferably 0 to 3, particularly preferably 0 to 1, very particularly preferably 0, i.e. all carbon atoms of the carbon ring are substituted by hydrogen, with the exception of a carbon atom which carries the amino group. Suitable radicals R' are, independently of one another, alkyl radicals which may be branched or unbranched and/or interrupted by one or more nitrogen atoms. The radicals R' are preferably $C_1$-$C_{20}$-alkyl radicals, particularly preferably $C_1$-$C_4$-alkyl radicals. Suitable alkyl radicals are, for example, methyl, ethyl, n- or iso-propyl, n- or iso- or tert-butyl.

The radicals R' can also, independently of one another, be cycloalkyl radicals which may be substituted by the above-mentioned functional groups or by alkyl, alkenyl or alkynyl groups and/or interrupted by one or more nitrogen atoms. Preferred cycloalkyl radicals have 3 to 13 carbon atoms—optionally partially replaced by nitrogen atoms—in their ring, particularly preferably 5 or 6 carbon atoms. The cycloalkyl radicals are very particularly preferably unsubstituted. Particularly suitable cycloalkyl radicals are, for example, cyclopentyl and cyclohexyl.

It is also possible for the radicals R', independently of one another, to be alkenyl radicals or alkynyl radicals which have one or more multiple bonds, preferably 1 to 4 multiple bonds. The alkenyl or alkynyl radicals can be substituted corresponding to the alkyl radicals or be interrupted by one or more nitrogen atoms.

It is also possible for two of the radicals R' to form a ring together which may be substituted in turn by alkyl, alkenyl or alkynyl groups.

Particularly preferably, the radicals R' are, independently of one another, methyl, ethyl or n- or isopropyl.

Among the listed compounds, enamines which are not further conjugated chosen from

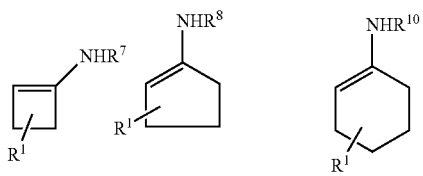

are very particularly preferred.

Preferred N-heterocyclic compounds in the form of imines or enamines are cyclic compounds with a total of 3 to 20 atoms, preferably 5 to 12 atoms, particularly preferably 5 to 7 atoms. In this connection, the N-heterocyclic compound can, in addition to the necessarily present nitrogen atom, contain further heteroatoms, preferably nitrogen atoms. The number of further heteroatoms is here dependent on the ring size. The N-heterocyclic compounds preferably contain no to 2 further heteroatoms, particularly preferably no or 1 further heteroatom above a ring size of 5 atoms. The carbon atoms of the N-heterocyclic compound can carry further radicals. Suitable radicals here are the same as those which have already been listed as radicals R' of the carbon rings of the abovementioned cyclic enamines. In the case of N-heterocyclic compounds which, in addition to the N atom, contain further heteroatoms, preferably nitrogen atoms, the heteroatoms, apart from a nitrogen atom, can carry further radicals R' in addition to the carbon atoms. In addition to the imine or enamine double bond, the N-heterocyclic compounds can have further double bonds which may be conjugated to give the imine or enamine double bond or may be nonconjugated. Preference is given to using N-heterocyclic compounds which have no conjugated double bonds.

Suitable N-heterocyclic compounds are, for example:

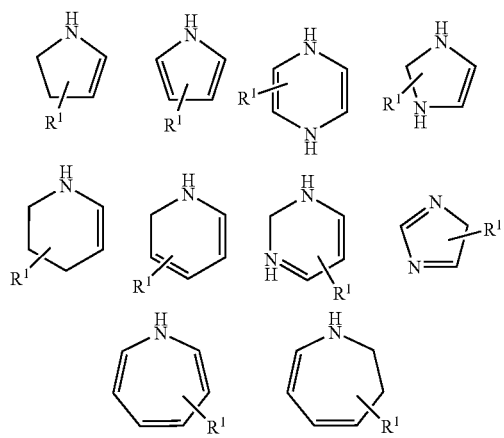

Here, the radical R' has the same meaning as the radical R' given in conjunction with the preferred cyclic enamines. R' is preferably 0 to the number of ring atoms minus 1, particularly preferably all ring atoms of the N-heterocyclic compounds carry hydrogen atoms or a radical R', where at least one nitrogen atom of the N-heterocyclic ring carries a hydrogen atom.

Among the listed compounds, N-heterocyclic compounds which have no conjugated double bonds chosen from

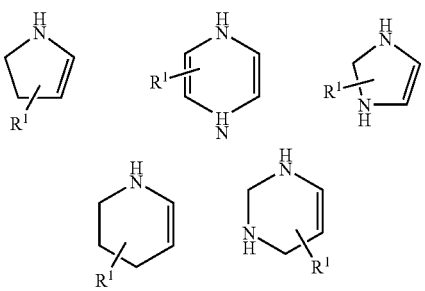

are particularly preferred.

Very particular preference is given to compounds of the following formula:

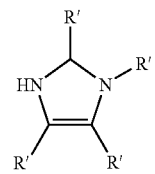

in which R' has the meaning given above.

The cocatalyst is particularly preferably an imine or tautomeric enamine compound which is formed during the dehydrogenation of the starting and/or product amine, or a degradation or secondary product of the corresponding imine or tautomeric enamine compound. The cocatalyst is very particularly preferably an imine or tautomeric enamine compound which is formed during the dehydrogenation of the starting amine, or a degradation or secondary product of the imine or tautomeric enamine compound.

It is possible to prepare the desired cocatalyst and to add it separately to the starting materials. It is, however, also possible to prepare the cocatalyst in situ before or during the reaction (hydroamination reaction). Here, in a preferred embodiment, the cocatalyst forms by reacting the hydride used as catalyst or the metal used for the catalyst preparation prior to the reaction with the alkene, with the mono- or dialkylamine chosen as starting amine (or optionally mono- or diarylamine or alkylarylamine), and removing the hydrogen formed from the reaction mixture. Preferably, a distillation of the mixture and subsequent separation into a gas phase, a low-boiling component fraction containing the starting amine and the cocatalyst, and a bottom fraction containing the hydride or the metal takes place. The low-boiling component fraction is then added to the bottom fraction, the procedure described is optionally repeated and the hydroamination is started by adding alkene and optionally further starting amine.

It is also possible to form the desired cocatalyst during the reaction. The cocatalyst is formed during the reaction here by reacting diethylamine with ethylene in the presence of a metal hydride or metal as catalyst, where the resulting reaction mixture is preferably separated by distillation into a gas phase (a), which comprises hydrogen and unreacted ethylene, a low-boiling component fraction (b), which comprises unreacted starting amine and the cocatalyst, a medium-boiling component fraction (c), which comprises product amine, and a bottom fraction (d) which comprises the catalyst. The fraction (b) is replenished with fresh starting amine and ethylene and returned to the bottom fraction which comprises the catalyst. In this connection, it is also possible to isolate the unreacted ethylene from the gas phase (a) and to return it together with the low-boiling component fraction (b) to the bottom fraction.

In a preferred embodiment, the process according to the invention is carried out such that hydrogen which forms during the reaction is removed from the reaction mixture. This can preferably be achieved by distillation or stripping. In addition, it must be taken into consideration that the residual substances separated off in the distillation are completely or partially returned to the process.

Without being bound to one theory, one possible mechanism which leads to the formation of the cocatalyst during the in-situ formation of the cocatalyst in the reaction of sodium hydride and diethylamine will be shown below. The proposed mechanism is valid both for the use of metal hydrides and also for the use of alkali metals for the preparation of the catalysts.

The reaction of sodium hydride with diethylamine forms very small amounts of $NaNEt_2$. This probably breaks down in accordance with the scheme below:

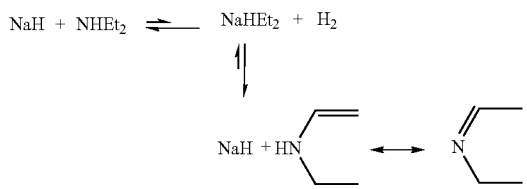

The enamine/imine which forms in the process has adequate acidity which is sufficient to permit protonation of the sodium hydride or oxidation of the metal to a high degree.

Alternatively or additionally, the imine can also be prepared by dehydrogenation of the starting amine in the presence of a hydrogenation/dehydrogenation catalyst, which is shown below:

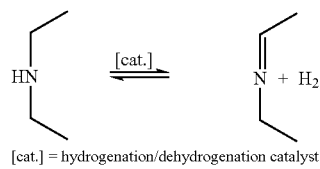

[cat.] = hydrogenation/dehydrogenation catalyst

Suitable hydrogenation/dehydrogenation catalysts are all customary hydrogenation/dehydrogenation catalysts. Use is generally made of transition metal catalysts in the form of unsupported or supported catalysts. Preferred transition metals are chosen from groups VIIb and Ib of the Periodic Table of the Elements. Particular preference is given to Fe, Ru, Co, Ni, Pd, Pt and Cu or alloys of these metals. Suitable support materials are, for example, carbon, $SiO_2$, $Al_2O_3$, $ZrO_2$ and $TiO_2$. Furthermore, the hydrogenation/dehydrogenation catalysts can comprise promoters/modifiers chosen from Sn, Sb, alkali metals, alkaline earth metals, Bi and Pb. Suitable hydrogenation/dehydrogenation catalysts are, for example, Raney-Ni, Raney-Cu, Raney-Co, Pd/$\gamma$-$Al_2O_3$, Pt/carbon, Ru/$SiO_2$, Pd/Sn/Cs/$\gamma$-$Al_2O_3$.

The exact compositions of suitable hydrogenation/dehydrogenation catalysts are known to the person skilled in the art.

In a preferred embodiment of the process according to the invention, the hydrogenation/dehydrogenation catalysts are introduced into a reactor together with the metal hydride or metal amide used as catalyst.

In a preferred embodiment of the process according to the invention, the hydrogen is removed from the system during the above-described reactions in order to shift the equilibrium further in the direction of the desired cocatalyst.

The present application thus further provides a novel process for the preparation of alkylamines (product amines) by reacting ethylene with diethylamine and dimethylamine in the presence of a metal hydride or metal amide as catalyst, where the reaction takes place in the presence of a cocatalyst.

In this process, the formation of the cocatalyst takes place in situ prior to the reaction of the diethylamine with the ethylene (hydroamination), or during the reaction of the diethylamine with the ethylene.

In addition, complexing agents may be present as solvent both during the catalyst preparation and also during the reaction.

Thus, for example, B. J. F. Remenar (J. Am. Chem. Soc. 120 (1988), 4081ff), H. Lehmkuhl et al. (J. Organomet. Chem. 55 (1973), 215ff and D. Steinborn et al. (Z. Chem. 29 (1989), 333ff describe the use of N,N,N',N'-tetramethylethylenediamine, N,N,N',N",N"-pentamethyldiethylenetriamine, N,N,N',N'-tetramethylcyclohexanediamine and tetrahydrofuran as complexing agents.

In addition, amines with two or more aminic N atoms per molecule, such as, for example, N,N,N',N'-tetraethylethylenediamine, N-permethylated or N-perethylated triethylenetetramine up to N-permethylated or N-perethylated polyimine with molar masses up to 500 000 daltons, ethers and polyethers, such as, for example diglymes, triglymes and the corresponding homologs, terminally capped polyols—e.g. PEG, PPG, poly-THF, and complexing agents with aminic N and etheric O atoms in the molecule, such as, for example, 3-methoxyethylamine, 3-(2-methoxyethoxy)propylamine or N,N,N',N'-tetramethyldiaminodiethyl ether, may be added to the reaction mixture.

The catalyst can be in the form of a solution, a suspension or supported on a typical catalyst support, such as, for example, $SiO_2$, $Al_2O_3$, $TiO_2$, $ZrO_2$, activated carbon, MgO, $MgAl_2O_4$. The catalyst is preferably in the form of a solution or suspension, particularly preferably in the form of a solution.

The hydroamination of ethylene can be carried out batchwise (addition of the olefin to catalyst and amine), semicontinuously (addition of the olefin to the reaction mixture) or continuously (addition of all components).

Preference is given in each case to a molar ratio of ethylene:secondary amine of 3:1 to 1:10, particular preference being given to 1:1 to 1:2.

Following the hydroamination reaction, the catalyst is separated off from the reaction mixture. This takes place by the customary methods, for example distillation under reduced or atmospheric pressure, filtration, membrane filtration, sedimentation, washing with water, preferably acids, salt solutions or alcohol.

Nonprotolyzed catalyst (metal alkylamide or metal hydride) can then be returned.

During the hydroamination, transalkylation reactions may produce by-products in addition to the desired products, for example trimethylamine or diethylmethylamine. This by-product formation can be suppressed by suitable reaction procedure, suitable choice of catalyst or amount thereof and further measures known to the person skilled in the art. The reaction is preferably carried out so that 0.5% by weight, preferably <0.3% by weight, in particular <0.1% by weight, of by-products arise as a result of transalklation.

In one embodiment of the present invention, the amine mixtures obtained after the catalyst has been removed are separated and some of the triethylamine is transalkylated in an isomerizing manner with the addition of ammonia. Following optional reseparation, the diethylamine formed is then returned as starting material. In this way, the process according to the invention can be designed flexibly and the product spectrum can be tailored to the requirements of the market.

The transalkylation, which is carried out under conditions known to the person skilled in the art, thus provides a starting amine for the hydroamination.

The isomerization/hydrogenation stage can optionally be designed as a reactive distillation.

The described reaction of the transalkylation of the amines is carried out at temperatures of from 80 to 400° C.

In particular, the reaction of the hydroamination product can take place under transalkylating conditions, as described, for example, in Houben Weyl volume XI/1, Nitrogen compounds II, 1957, Georg Thieme Verlag Stuttgart, p. 248 to 261.

Accordingly, the amine transalkylation ("amine exchange") will be carried out in the presence of dehydration catalysts and hydrogenation/dehydrogenation catalysts.

Dehydration catalysts suitable as transalkylation catalysts are disclosed, for example, in the application DE 101 55 524.5 by the applicant dated Nov. 12, 2001. The transalkylation catalysts disclosed in this application are an integral part of the present invention and incorporated by reference.

length of the alkyl groups. The more sterically demanding the alkyl groups, the lower the proportion of the corresponding tertiary alkylamine.

The space velocity over the catalyst with the starting material can be between 0.05 and 2 kg of starting material per liter of catalyst and per hour (kg/l*h), preferably between 0.1 and 1 kg/l*h, particularly preferably between 0.2 and 0.6 kg/l*h.

The molar ratio of the resulting amines relative to one another can be varied in wide ranges depending on the desired product mix. After releasing the pressure, the discharge can be distilled off and diethylamine returned, or triethylamine removed as product. Any monoethylamine which forms is removed from the reaction cycle. Ammonia can be returned to the transalkylation.

EXAMPLE 1

Synthesis of Ethyldimethylamine and Triethylamine

In a 250 ml autoclave, sodium diethylamide (50 mmol) and the diethylamide/dimethylamide mixture (5 mol/2 mol) was introduced into the reactor under a gentle stream of argon. With stirring, the reactor was brought to the operating temperature (70° C.) and then 40 bar of ethene were injected. During the experiment, the reaction pressure was kept at 40 bar with ethene and samples were taken. At the end of the experiment, the autoclave was cooled, decompressed and the residual catalyst was deactivated with ethanol.

GC analysis: 50° C. (5 min) −15° C./min −280° C. (25 min). The run sample was taken via a riser pipe, the initial charge was cooled with $CO_2$ and the sample was then treated with 50 percent KOH. Further details are summarized in Table 1.

TABLE 1

Addition of DMA (2 mol)/DEA (5 mol) onto ethene 70° C., 40 bar, cat: 50 mmol $NaNEt_2$

| | GC - analysis area % | | | | | | |
|---|---|---|---|---|---|---|---|
| Time min | N-Ethyl-dimethylamine % Rt = 4,588 | Triethylamine % Rt = 8,675 | Internal in ° C. Room temperature | Jacket in ° C. | Pressure In bar | Ethene g of feed | Ethene g of uptake |
| 0 | 0 | 2.6 | 67.5–85.7 | 79.0 | 0–20 | 0–30.6 | in 1 min |
| 10 | | | 72.0–77.0 | 70.0 | 2–20 | 54.8 | in 1 min |
| 15 | 18.28 | 6.54 | 77.3 | 69.6 | 10 | 57.0 | 2.2 |
| 30 | 22.89 | 14.35 | 69.5 | 79.1 | 42.0 | 140.5 | 83.5 |
| 60 | 22.27 | 25.89 | 71.4 | 76.0 | 42.0 | 161.5 | 21.0 |
| 90 | | | 71.4 | 75.8 | 42.0 | 177.2 | 15.7 |
| 120 | 20.89 | 38.59 | 69.2 | 77.0 | 40.0 | 182.9 | 5.7 |
| 180 | 19.61 | 48.84 | 70.9 | 75.3 | 41.5 | 205.2 | 22.3 |
| 240 | | | 70.6 | 76.2 | 43.0 | 224.9 | 19.7 |
| 270 | 18.78 | 60.09 | 70.6 | 75.9 | 43.0 | 228.0 | 3.1 |
| 360 | 17.98 | 66.68 | 69.1 | 76.3 | 43.0 | 245.5 | 17.5 |

For a reaction in the gas phase the pressure is generally 1 to 70 bar.

For a reaction in the liquid phase, the pressure is generally 70 to 250 bar.

The temperature is generally 80 to 400° C., in particular between 100 and 350° C., preferably between 120 and 250° C., very particularly preferably between 150 and 230° C.

Depending on the temperature chosen, an equilibrium of the alkylamine plus optionally ammonia is established which depends on the ratio of the nitrogen to steric stress and The evaluation of the experiment shows that the addition of ethylene onto dimethylamine proceeds more rapidly than the corresponding addition onto diethylamine. Dimethylethylamine is formed within a short period (30 min). The formation of triethylamine is also still not completely concluded after 360 min.

EXAMPLE 2

Comparison of the Activity of Diethylamide and Dimethylamide in the Synthesis of Triethylamine In a 1 l autoclave, Na dimethylamide and Na diethylamide (in each case 60 mmol) and diethylamine (450 g, 6.08 mol)

was introduced into the reactor under a gentle stream of argon. With stirring, the reactor was brought to the operating temperature (70° C.) and then 40 bar of ethene were injected. During the experiment, the reaction pressure was kept at 40 bar with ethene and samples were taken. At the end of the experiment, the autoclave was cooled, decompressed and the residual catalyst was deactivated with ethanol.

GC analysis: capillary column 30 m long, 1.5 μm, 0.32 mm Rtx-5-amine temp. program: 50° C. (5 min) –15° C./min –280° C. (25 min). The run sample was taken via a riser pipe, the initial charge was cooled with $CO_2$ and the sample was then treated with 50 percent KOH.

The evaluation of the experiment shows that the conversion of the reaction using sodium dimethylamide is higher than the corresponding reaction catalyzed with sodium diethylamide. Since sodium dimethylamide is very much more stable than Na diethylamide, decomposition to give the hydride is also slowed. In the same time, more can thus be converted by the much more active amide.

TABLE 2

Triethylamine synthesis at 40 bar, 70° C., catalyzed with 60 mmol of sodium dimethylamide

| Time | GC analysis area % | | | Internal | Jacket | Pressure | Ethene | Ethene |
|---|---|---|---|---|---|---|---|---|
| min | DEA | TEA | DEA + TEA | in ° C. | in ° C. | in bar | g of feed | g of uptake |
| Triethylamine synthesis: 40 bar, 70° C., catalyzed with 60 mmol of sodium diethylamide | | | | | | | | |
| 0 | Start | | | 68.1 | 80.7 | 0–38 | 98.3 | in 10 min |
| 15 | 88.59 | 5.48 | 94.07 | 68.2 | 79.8 | 40.0 | 106.4 | 8.1 |
| 30 | 85.88 | 11.94 | 97.82 | 71.0 | 77.8 | 40.0 | 120.8 | 14.4 |
| 60 | 75.75 | 20.29 | 96.04 | 70.6 | 77.8 | 40.0 | 138.2 | 17.4 |
| 120 | 60.62 | 34.21 | 94.83 | 71.3 | 77.2 | 39.0 | 157.2 | 19.0 |
| 150 | | | | 70.9 | 76.7 | 39.0 | 171.5 | 14.3 |
| 180 | | | | 70.6 | 76.5 | 39.0 | 179.0 | 7.5 |
| 240 | 48.05 | 48.60 | 96.65 | 70.6 | 77.7 | 39.0 | 187.0 | 8.0 |
| 360 | 39.87 | 54.84 | 94.71 | 70.5 | 76.3 | 39.0 | 192.0 | 5.0 |
| Triethylamine synthesis: 40 bar, 70° C., catalyzed with 60 mmol of sodium dimethylamide | | | | | | | | |
| 0 | Start | | | 71.5 | 75.7 | 0–38 | 74.0 | in 2 min |
| 15 | 88.52 | 6.12 | 94.64 | 69.5 | 83.5 | 42.0 | 106.0 | 32.0 |
| 30 | 85.91 | 9.93 | 95.84 | 72.6 | 76.7 | 40.0 | 117.0 | 11.0 |
| 60 | 75.39 | 18.74 | 94.13 | 72.4 | 74.8 | 41.0 | 135.3 | 18.3 |
| 120 | 65.44 | 31.24 | 96.68 | 71.3 | 73.6 | 40.5 | 158.3 | 23.0 |
| 150 | | | | 71.4 | 73.5 | 40.5 | 171.2 | 12.9 |
| 180 | | | | 71.0 | 74.3 | 40.5 | 177.4 | 6.2 |
| 240 | 51.25 | 46.46 | 97.71 | 70.8 | 73.9 | 40.5 | 186.0 | 8.6 |
| 360 | 44.99 | 51.74 | 96.73 | 70.7 | 74.4 | 40.5 | 204.1 | 18.1 |

We claim:

1. A process for the preparation of ethyldimethylamine and triethylamine with the following steps
    (i) reaction of a mixture of diethylamine and dimethylamine with ethylene in the presence of a catalyst from the group of alkali metal dimethylamides, alkali metal diethylamides and alkali metal hydrides
    (ii) removal of the catalyst
    (iii) distillation separation of the resulting mixture in triethylamine and ethyldimethylamine and optionally diethylamine and dimethylamine
    (iv) optional return of the catalyst and of the starting amines to the reaction.

2. A process as claimed in claim 1, wherein diethylamine is used in excess.

3. A process as claimed in claim 2, wherein the diethylamine/triethylamine ratio is (8 to 15):1.

4. A process as claimed in claim 3, wherein the diethylamine/triethylamine ratio is 10:1.

5. A process as claimed in claim 1, wherein ethylene is used in excess.

6. A process as claimed in claim 1, wherein the alkali metal is chosen from Li, Na or K.

7. A process as claimed in claim 6, wherein the alkali metal is chosen from Na.

8. A process as claimed in claim 1, wherein the catalyst is chosen from Na diethylamide or Na dimethylamide or mixtures thereof.

9. A process as claimed in claim 1, wherein the metal amide is prepared prior to use in the reaction from dimethylamine or diethylamine or a mixture thereof in a manner known per se.

10. A process as claimed in claim 1, wherein the streams passed to the reactor comprise 0 to 1% by weight of ammonia, 0 to 5% by weight of (monoethylamine+monomethylamine), 20 to 80% by weight of (diethylamine+dimethylamine), 0 to 50% by weight of triethylamine, 5 to 50% by weight of ethylene, 0.01 to 20% by weight of the catalyst and 0 to 20% by weight of a solvent for the catalyst.

11. A process as claimed in claim 10, wherein the streams passed to the reactor comprise <0.1% by weight of ammonia, <1% by weight of (monoethylamine+monomethylamine), 40 to 70% by weight of (diethylamine+dimethylamine), <40% by weight of triethylamine, 10 to 30% by weight of ethylene and 0.1 to 2% by weight of the catalyst.

12. A process as claimed in claim 1, wherein the preparation of the amide and the hydroamination are carried out in a single process stage.

13. A process as claimed in claim 1, wherein a cocatalyst from the group of cyclic or open-chain imine or of tautomeric enamine compounds is used.

14. A process as claimed in claim 1, wherein some of the amine mixture obtained following removal of the catalyst is separated, some of the triethylamine is transalkylated in an isomerizing manner with the addition of ammonia, and the resulting diethylamine, following removal, is returned as starting material to the reactor.

* * * * *